United States Patent
Turnbull et al.

[11] Patent Number: 5,833,674
[45] Date of Patent: Nov. 10, 1998

[54] NEEDLELESS IV MEDICAL DELIVERY SYSTEM

[75] Inventors: Christopher J. Turnbull, St. Paul; Richard L. Globensky, Anoka, both of Minn.

[73] Assignee: St. Paul Medical, Inc., Minneapolis, Minn.

[21] Appl. No.: 586,784

[22] PCT Filed: Aug. 27, 1993

[86] PCT No.: PCT/US93/08045

§ 371 Date: Feb. 1, 1996

§ 102(e) Date: Feb. 1, 1996

[87] PCT Pub. No.: WO95/05863

PCT Pub. Date: Mar. 2, 1995

[51] Int. Cl.⁶ ................................................. A61M 25/00
[52] U.S. Cl. .......................... 604/283; 604/905; 604/86; 604/244; 604/256
[58] Field of Search .................................. 604/83, 86, 89, 604/167, 169, 88, 91, 239, 240, 243, 244, 256, 283, 284, 411–415, 905, 165

[56] References Cited

U.S. PATENT DOCUMENTS

| | | |
|---|---|---|
| Re. 33,617 | 6/1991 | Ogle, II . |
| 3,976,073 | 8/1976 | Quick et al. . |
| 4,005,710 | 2/1977 | Zeddies et al. . |
| 4,121,585 | 10/1978 | Becker, Jr. . |
| 4,607,671 | 8/1986 | Aalto et al. . |
| 4,610,469 | 9/1986 | Wolff-Mooij . |
| 4,624,667 | 11/1986 | Rutnarak ................................. 604/414 |
| 4,655,762 | 4/1987 | Rogers . |
| 4,752,292 | 6/1988 | Lopez et al. . |
| 4,759,756 | 7/1988 | Forman et al. . |
| 4,834,716 | 5/1989 | Ogle, II . |
| 4,874,377 | 10/1989 | Newgard et al. ........................ 604/167 |
| 4,935,010 | 6/1990 | Cox et al. . |
| 4,964,855 | 10/1990 | Todd et al. . |
| 5,047,021 | 9/1991 | Utterberg ................................. 604/283 |
| 5,100,394 | 3/1992 | Dudar et al. . |
| 5,167,648 | 12/1992 | Jepson et al. . |
| 5,171,234 | 12/1992 | Jepson et al. . |
| 5,178,607 | 1/1993 | Lynn et al. ................................. 604/86 |
| 5,188,620 | 2/1993 | Jepson et al. . |
| 5,199,947 | 4/1993 | Lopez et al. . |
| 5,199,948 | 4/1993 | McPhee ..................................... 604/86 |
| 5,251,873 | 10/1993 | Atkinson et al. . |
| 5,342,315 | 8/1994 | Rowe et al. ............................. 604/167 |
| 5,354,275 | 10/1994 | Behnke et al. . |
| 5,405,331 | 4/1995 | Behnke et al. . |
| 5,509,911 | 4/1996 | Cottone, Sr. et al. .................. 604/283 |

*Primary Examiner*—Ronald Stright, Jr.
*Assistant Examiner*—Cris L. Rodriguez
*Attorney, Agent, or Firm*—Haugen and Nikolai, P.A.

[57] ABSTRACT

An injection site and unsharpened drug transfer spike for facilitating coupling a syringe to a fluid line. The injection site has a uniquely designed housing and septum comprised of only two parts. The drug transfer spike has a positive locking member for restricting retraction from the injection site once it is inserted for injecting a medicant. The positive locking member preferably comprises a annular ridge defined about the shaft of the drug transfer spike. The septum includes a pair of axially aligned, oppositely oriented conical recesses with adjacent apices either separated by a thin membrane or intersecting at the time of manufacture. The housing has an inlet for receiving the septum and comprises a plurality of fingers with inwardly extending tabs for constraining the septum therewithin. The septum is ideally adapted to be applied to injection sites, Y-connectors, vial adaptors, single or multi-dose vials and blood collection tubes. When the drug transfer spike is made to penetrate the septum, the walls of the septum or the inwardly extending tabs tightly engage the shaft of the spike to preclude inadvertent withdrawal.

23 Claims, 3 Drawing Sheets

NEEDLELESS IV MEDICAL DELIVERY SYSTEM

I. FIELD OF THE INVENTION

The present invention relates generally to medical systems for administering fluids to a patient, and more particularly to a plurality of components incorporating an injection site, including a preformed elastomeric, self-sealing septum, for receiving a syringe needle or a relatively blunt drug delivery spike.

II. BACKGROUND OF THE INVENTION

The administration of fluids to a patient is typically accomplished by inserting a catheter into a patient's vein, and then coupling a source of fluid thereto using an administration set including flexible tubing and one or more couplings or fittings. Occasionally, medication is prescribed by a physician and administered by injecting a dosage of the medication from a syringe into the catheter. This can be accomplished by temporarily disconnecting the catheter from the source of fluid and then coupling the syringe to the catheter.

Alternatively, Y-connectors are customarily incorporated in the administration set to merge fluids from two or more sources to a common tube and to the patient. A typical Y-connector has a self-sealable inlet at one branch, known as an injection site, through which the tip of a piercing member can penetrate for injecting medication. The source of fluid is coupled to a second branch of the Y-connector and remains connected while administering the medication via the first branch. These injection sites usually include an elastomeric plug, sometimes referred to as a "septum" to form a liquid seal.

To avoid accidental sticking while administrating a dosage to the Y-connector, a drug transfer spike, comprised of a cannula is typically attached to the syringe in place of a conventional hypodermic needle. The drug transfer spike has a blunt tip which is adapted to pierce and penetrate the sealable inlet or septum at the injection site. By implementing pre-slit septums in combination with drug transfer spikes having blunt tips, accidental punctures which might otherwise result from the use of a standard syringe having a sharp-tipped hypodermic needle are avoided.

In U.S. Pat. No. 5,199,948 to McPhee, a needleless valve is disclosed having a pre-slit septum. The septum is held in place in a housing inlet by a cap affixed thereabout. The septum disclosed has a concave upper surface which bulges and flattens when disposed in the housing inlet and retained by the cap. A drug transfer spike is disclosed having a ball-shaped tip, pointed enough to penetrate the diaphragm of a drug vial, but which is not sharp enough to puncture human skin. The McPhee injection set comprises a total of three pieces. It does not include a locking mechanism for restricting accidental withdrawal of the drug transfer spike from the septum of the injection site.

U.S. Pat. No. 5,167,648 to Jepson et al. also teaches a pre-slit injection site and an associated cannula. A resealable septum is disposed in a cylindrical housing having tapering interior walls and the outer surface of the septum is forced into a dome-like shape due to axial forces applied to the septum's perimeter by the housing's swaged end members. The septum disclosed includes an elastomeric disc with a zero-clearance slit defined axially therethrough.

OBJECTS

It is accordingly a principle object of the present invention to provide an improved injection site for components used in administration sets, which will reliably seal about a blunt tipped drug delivery pin or cannula when pierced.

Another object of the invention is to provide in combination an elastomeric injection site septum and a blunt tipped drug delivery pin or cannula where the pin or cannula includes a means for locking itself to the injection site.

It is a further object of the present invention to provide an injection site comprised of a minimal number of parts, and of parts which can be easily and inexpensively manufactured.

Still another object of the present invention to provide an injection site which can be incorporated into a variety of devices including extension tubes, Y-connectors, vial adaptors, PRN adaptors, single or multi-dose medicament containers, blood collection tubes and fluid source bags.

SUMMARY OF THE INVENTION

The foregoing objects and advantages of the present invention are achieved by a providing a injection site on a variety of components, the injection site including a preformed septum constrained within a housing inlet, and used in combination with a drug transfer spike, the transfer spike having a locking mechanism disposed along the length thereof for restricting retraction of the drug transfer spike from the septum when inserted therethrough.

More specifically, the injection site comprises a right circular cylindrical body formed from natural rubber or a suitable elastomeric material having a pair of conic recesses inverted relative to one another and coaxially aligned with their apices either separated from each other by a relatively thin membrane prior to its being pierced or intersecting to create a small opening which becomes closed when the body is compressed into a housing. The septum is received and constrained within a molded plastic housing. An elongated drug transfer spike or cannula is provided which is adapted to be axially inserted through the septum membrane into the housing. The drug transfer spike has a first female Luer at one end adapted to mate with a syringe or a male Luer on a different apparatus, an outlet port at the other end adapted to be inserted through the conical septum opening or membrane, and a tubular midsection with a passageway joining the Luer fitting and the outlet port to one another. The drug transfer spike also has a locking mechanism disposed on a peripheral surface thereof for restricting retraction of the drug transfer spike from the septum when inserted therethrough. Preferably, the locking mechanism is a positive locking member comprised of a protrusion, preferably in the form of a ring extending outwardly from the transfer spike at a predetermined location. In one arrangement, this annular protrusion can be forced through the septum to provide a tight friction engagement therewith, wherein a substantial amount of force is required to retract the drug transfer spike from the injection site due to the protrusion's engagement with the septum walls. Alternatively, the annular protrusion can be located on the spike at a location where it will be engaged by the plastic housing in which the septum is inserted.

The housing inlet of the injection site is comprised of a generally cylindrical cavity defined by a plurality of housing fingers extending thereabout. Each finger is separated from the next by a narrow slot. Thus, each finger can be flexed slightly outwardly to receive the resilient septum therein during assembly. Each finger has an inwardly extending tab at a distal end thereof to constrain the septum within the housing inlet or recess. In a preferred embodiment, the resilient septum has a diameter slightly greater than the diameter of the housing inlet and is thus compressed when inserted into the housing inlet. Once inserted into the housing inlet, the septum engages the inlet walls in a friction arrangement. The height of the cylindrical cavity is such that the septum is not axially compressed.

Other objects and features of the present invention will become apparent to those skilled in the art through the Description of the Preferred Embodiment, claims, and Drawings herein, wherein like numerals in the various figures refer to like elements.

BRIEF DESCRIPTION OF THE DRAWINGS

FIG. 5 is a sectional view of an assembled tubular extension body having a male Luer lock on a lower end and a septum housing at its opposite end;

FIG. 6 is a sectional view of the tubular extension body shown in FIG. 5 adapted to a catheter at a lower end thereof, and receiving the drug transfer spike or cannula through the resilient septum, with the locking protrusion engaging surfaces thereof;

DESCRIPTION OF THE PREFERRED EMBODIMENT

Figure 1:
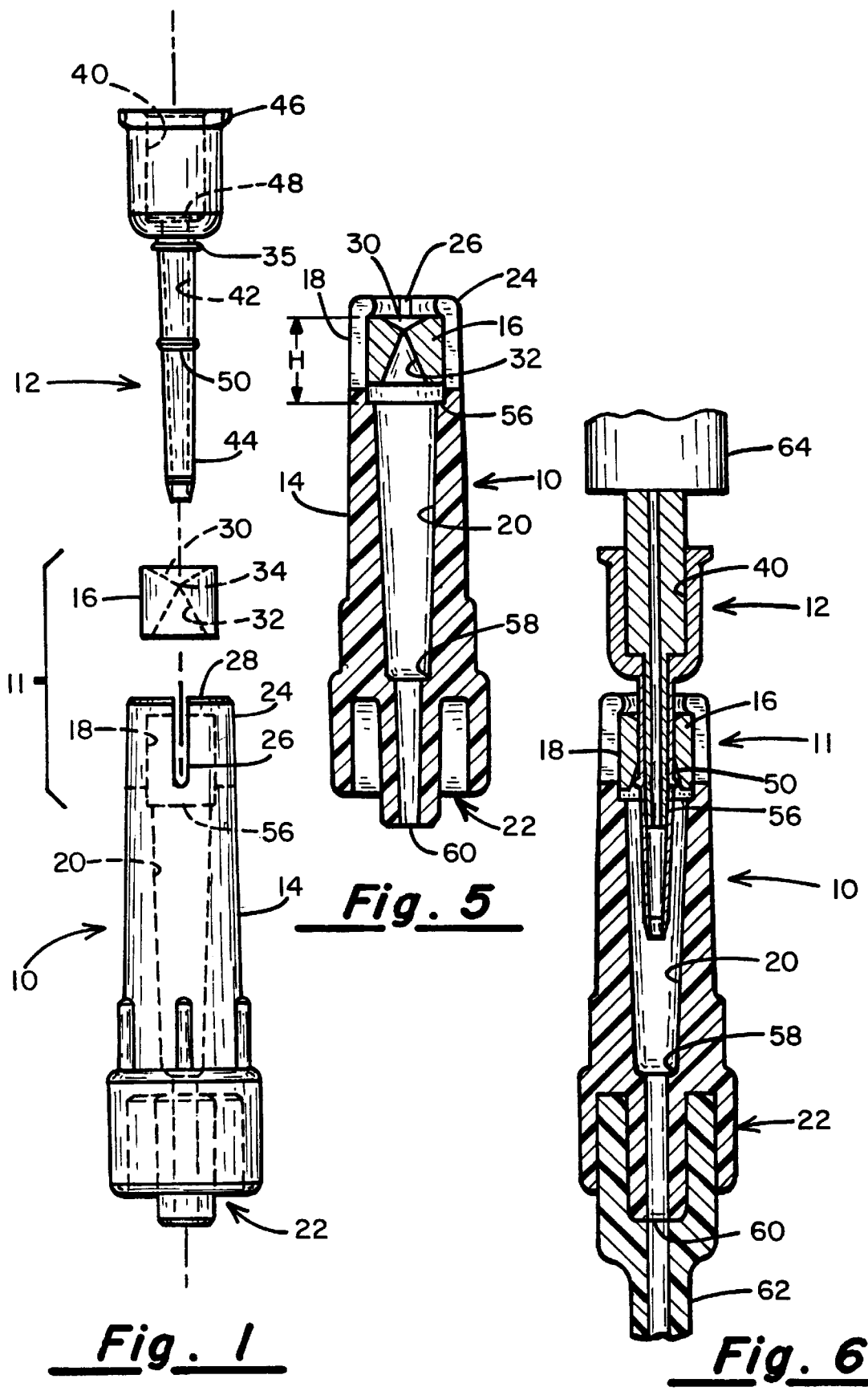
FIG. 1 is an exploded elevational view in greatly enlarged scale of an injection site contained within a tubular extension member adapted to receive a drug transfer spike or cannula, which cannula has a locking member or protrusion defined therealong for restricting retraction once inserted through the septum.

Referring now to FIG. 1, an exploded view of an injection site tube 10, termed a C-Lok, having an injection site 11 on the proximal end thereof and a drug transfer spike, herein termed a "key", adapted to be received therein is shown generally at 12. Injection site 11 comprises two pieces including an elongated injection tube 14 and a resilient cylindrical septum 16 adapted to be received in an inlet recess 18 defined at the upper or proximal end thereof. Injection tube 14 has a tapered lumen 20 extending axially therethrough, tapering from recess 18 to an integrally formed male Luer lock 22. The key 12 is adapted to mate with the tapered nose of a syringe which is in a fluid communication with lumen 20 of the injection tube 14.

Drug transfer spike or key 12 and injection tube 14 are preferably formed of a medical grade plastic, such as a polycarbonate. Thus, both parts can be manufactured using conventional molding techniques and are of an inexpensive material.

Injection tube 14 is particularly characterized in that recess 18 is surrounded by a plurality of fingers 24 extending upwardly in the axial direction at a proximal end thereof. Fingers 24 are defined by a plurality of equally spaced narrow slots 26 extending in the axial direction from the upper or proximal end of injection tube 14 towards its main body. Each finger 24 is further characterized as having a tab 28 at a proximal end thereof extending radially inward towards the axis of injection tube 14 to further define inlet or recess 18. Slots 26 may be positioned at 90° intervals but limitation to four fingers is not intended. Each finger 24 can be flexed outwardly to receive the cylindrical resilient septum 16 in recess 18. (See FIG. 5).

Septum 16 may be made from an elastomeric material preferably of a natural rubber material or a thermoplastic rubber having a durometer or hardness in the range of from 10 to 70 shore A. A silicone plastic may also be used if produced using a liquid injection molding (LIM) technique. It has a pair of axially aligned recesses defined therein. An upper recess 30 and the lower recess 32 each have a generally conical shape and are oriented with their apices adjacent one another. In one design, the apices are separated from one another by a thin membrane 34 at the time of manufacture. Alternatively, the apices may intersect to create a small diameter opening. Membrane 34 is adapted to be pierced when a drug transfer spike 12 is pushed through it, but provides a liquid-tight seal thereabout. (See FIG. 6.) Septum 16 provides a liquid-tight seal after drug transfer spike 12 is removed as well due to its resilient properties. Lower conic recess 32 is preferably larger than upper conic recess 30 to create a tight liquid seal at the location of membrane 34 or the preformed opening.

Figure 2:
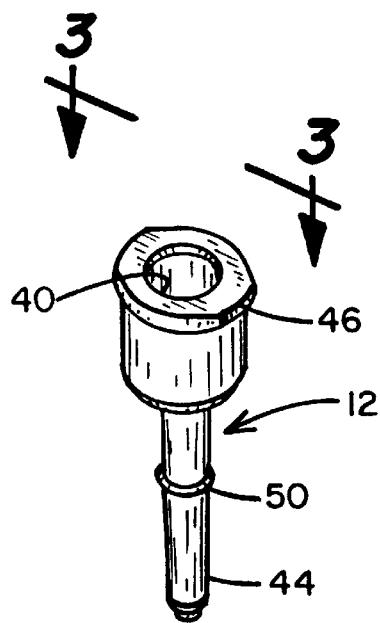
FIG. 2 is a perspective view of the drug transfer spike shown in FIG. 1 further illustrating the locking member or protrusion, and the upper portion of the spike comprised of a female Luer lock.

Referring to FIGS. 1 and 2, drug transfer spike 12 is comprised of a cannula with an axial passage or socket 40 defined at an upper end thereof. A tapered lumen 42 extends downwardly in the axially direction from socket or recess 40 to a distal end 44. Socket 40 and lumen 42 are adapted to receive a standard syringe. More particularly, drug transfer spike 12 includes a female Luer lock 46 as the socket 40. The bottom wall of socket 40 creates an annular shoulder 48 which abuts the distal nose of a conventional syringe when disposed therein. (See FIG. 6.) Drug transfer spike or key 12 is further characterized as having a positive locking member in the form of an annular protrusion 50 disposed at a predetermined position along the length of the drug transfer spike 12. As will be described below, when protrusion 50 is located approximately midway along its length, its rounded surface restricts retraction of the drug transfer spike 12 from the injection site 10 when the spike has been inserted through the membrane 34 so as to engage the side walls defining the conic recess 32. In an alternative arrangement, the annular protuberance is located a short distance from the bottom of the female Luer, as at 35 in FIG. 1, so as to interact with the finger tabs 28 to provide a locking detent.

Figure 3:
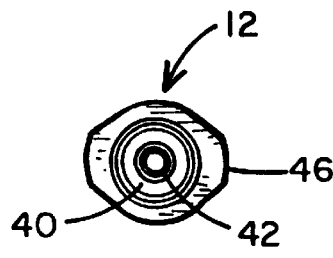
FIG. 3 is an end view 3—3 shown in FIG. 2 further illustrating the female Luer lock.

FIG. 3 is included to show an end view of drug transfer spike or key 12 and revealing the concentric features thereof.

Figure 4:
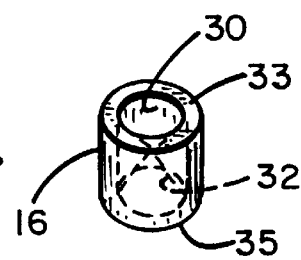
FIG. 4 is a perspective view of the resilient septum illustrated in FIG. 1 having a pair of axially aligned, oppositely oriented conical recesses with adjacent apices forming a narrow opening or a membrane.

Referring to FIG. 4, a perspective view of the elastomeric septum 16 is shown, illustrating the upper conical recess 30 and the lower conical recess 32 in phantom lines. As shown, septum 16 has narrow annular rims 33 and 35 defined at each end encompassing the respective recesses.

Referring now to FIG. 5, an assembled C-Lok 10 is shown with a septum 16 disposed within its 18. By way of example and without limitation septum 16 may have a diameter of approximately 0.250 inches which is slightly greater than the diameter of recess 18, which may be, for example, 0.216 inches. Thus, when installed as shown, resilient septum 16 is radially compressed slightly and thus elongated slightly in the axial direction. Cylindrical recess 18 has a height dimension H, wherein H may be approximately 0.296 inches. When installed in recess 18, septum 16 occupies generally 75% of that recess 18 by volume. Recess 18 has a generally cylindrical wall which extends downwardly to an annular shoulder 56. As shown, tapered passageway 20 tapers downwardly in the axial direction from shoulder 56 to an annular shoulder 58. Passageway 20 tapers downwardly from shoulder 58 to a lower port 60 forming a portion of male Luer lock 22.

FIG. 6 illustrates a sectional assembled view of injection site or C-Lok 10 and its housing 14 receiving drug transfer spike or key 12. A standard tubular catheter 62 is shown coupled to the male Luer lock 22, and a standard syringe 64 has its tapered nose disposed within conforming socket or recess 40 and passageway 42 of key 12. As shown, key 12 is inserted through membrane 34 of septum 16 such that positive locking member or protrusion 50 is disposed through the opening made through membrane 34 of septum 16 and frictionally engages the sloping surfaces of lower recess 32. Annular protrusion 50 inhibits the accidental or inadvertent retraction of drug transfer spike 12 from injection site 10.

When key 12 is inserted into injection site or C-Lok 10, septum 16 is further compressed in the radial direction such that septum 16 becomes even more elongated in the axial direction, as shown. Septum 16, however, still remains slightly spaced above shoulder 56 such that it is not axially compressed. As shown, because of its resilient properties, septum 16 maintains a liquid-tight seal about the key 12 for inhibiting leakage of medication from passageway 20. A substantial portion of housing passageway 20 remains unoccupied by the lower end of drug transfer spike 12, which unoccupied area can be utilized to receive a filter element if desired. Such a filter will prevent any particles scraped from the elastomeric septum from entering a patient.

In use, after a dose of medication has been withdrawn from a multiple dose or single dose vial, it can be ejected from syringe 64 into C-Lok 10, via injection site 11. Spike 12 and syringe 64 may then be retracted in the axial direction, either individually or together, from septum 16. Septum 16, being resilient, will return to its normal shape, shown in FIG. 5, such that a liquid-tight seal is again maintained by septum 16. Inwardly extending tabs 28 of fingers 24 constrain and restrict septum 16 from becoming dislodged while the drug transfer spike or key 12 is pulled out of the septum 16.

Figure 7:
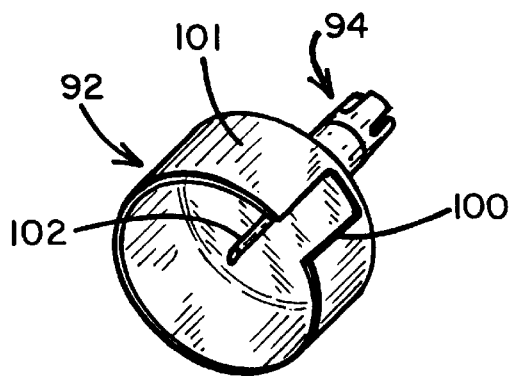
FIG. 7 is a perspective view of a vial adaptor which has an injection site including a septum according to the present invention.
Figure 9:
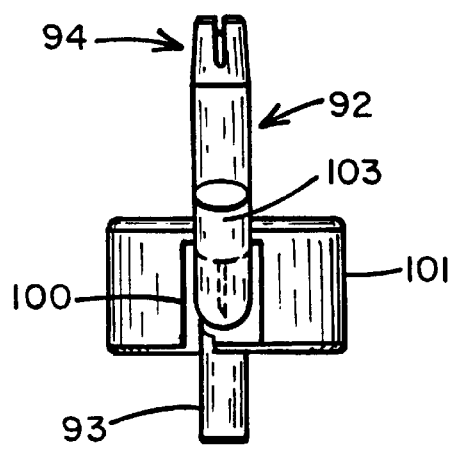
FIG. 9 is an elevational view of the vial adaptor shown in FIG. 7 adapted to a standard Y-connector.

Referring now to FIG. 7, a perspective view of a Key-Loc adaptor 92 is shown. The Key-Loc adapter is a single-patient, multi-use adapter device for gaining entrance to non-prepierced or self-sealing membranes, including elastomeric injection sites on intravenous tubing sets, the injection site on IV fluid bags and the membrane on single-dose and multi-dose medicament vials and the blood collection tubes/containers. FIG. 9 shows the Key-Loc adaptor 92 operatively coupled to a standard Y-connector 93 where a notch 100 in the shroud 101 accommodates one of the Y branches 103. The notch 100 extends from the edge of the cylindrical outer wall in the axial direction and is adapted to receive one of the Y branches. A stainless steel hypodermic needle 102 (FIG. 7) is concentrically disposed within the skirt or shroud 101 of the adaptor and recessed from its edge so as to be shielded to prevent accidental sticks of medical personnel who may handle it. In this configuration, adaptor 92 is adapted to receive a syringe and drug transfer spike or key at injection site 94.

A modified Y-connector is shown at 70 (FIG. 8) having a main branch 72 connected to an IV line 73 and a pair of bifurcated branches 74 and 76. Branch 74 is also coupled to an IV line 75. The branch 76 is aligned with the main branch 72 and has an injection site 80 similar in design to the upper end 11 of C-Lok 10 illustrated in FIGS. 1, 5 and 6. Specifically, injection site 80 includes a plurality of fingers 82 each having a septum retaining tab 84 extending radially inward, similar to fingers 24 and tabs 28 shown in FIG. 1. An inlet recess or socket 86 is formed at the proximal end of branch 76 for receiving a cylindrical, molded septum 16. Septum 16 and recess 86 may have the same dimensions as septum 16 and recess 18 previously described in reference to FIG. 1. Thus, key 12 can be locked to injection site 80 in either of the ways previously described in reference to FIG. 6.

Figure 8:
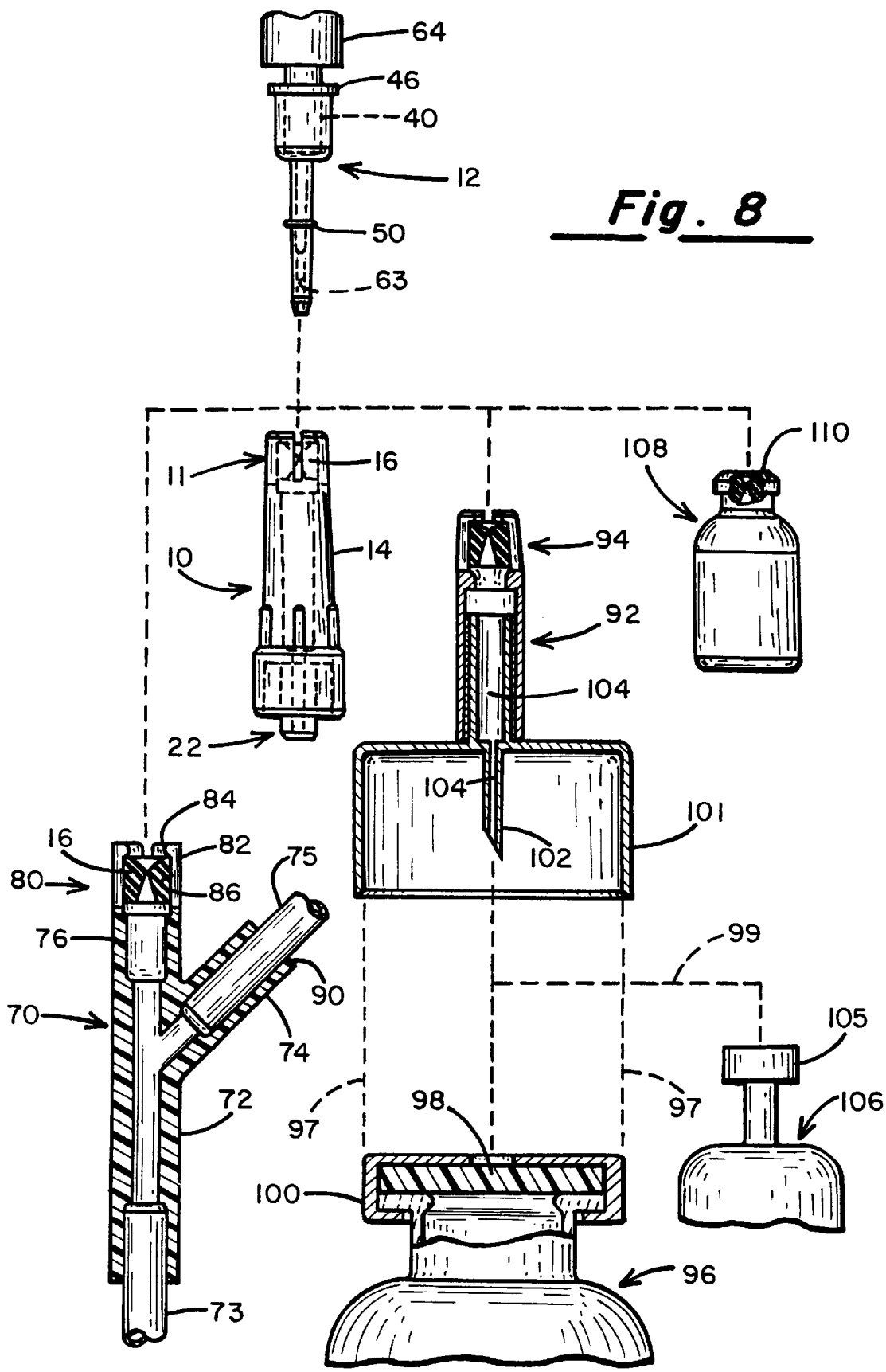
FIG. 8 is a greatly enlarged exploded drawing showing various devices incorporating the injection site according to the present invention and adapted to receive the disclosed drug transfer spike.

Still referring to FIG. 8, yet another feature of the present invention is shown. Here, the adaptor, indicated generally by numeral 92 has an injection site 94 similar to injection site 11 shown in FIG. 1. Adaptor 92 can be used with either a multi-dose vial 96 of medicant as is indicated by dashed lines 97, as shown, or to a single dose vial (not shown). A multi-dose vial may incorporate a conventional rubber barrier 98. Barrier 98 of vial 96 is disc-shaped and also comprised of a resilient natural or synthetic rubber material of a predetermined durometer. Septum 98 is adapted to be placed upon the rim of vial 96 and secured thereto using an industry standard aluminum seal ring 100. Adaptor 92 has a sharpened metal needle 102 with a lumen 104 axially extending therethrough.

Needle 102 is adapted to penetrate through septum 98, or a standard rubber seal 105 of IV bag 106 as indicated by the dashed lines 99 in FIG. 8. Alternatively, Key-Lok adaptor 92 can be used in combination with a key 12 to couple syringe 64 to a standard IV fluid bag, shown at 106.

In yet another arrangement, the syringe 64 and spike 12 may be used to enter a single or multi-does vial 108 if this vial is provided with an elastomeric barrier 110 having the inverted conical recesses similar to those on the septum of an injection site, making it unnecessary to use adaptor 92 to load the syringe.

Figure 10:
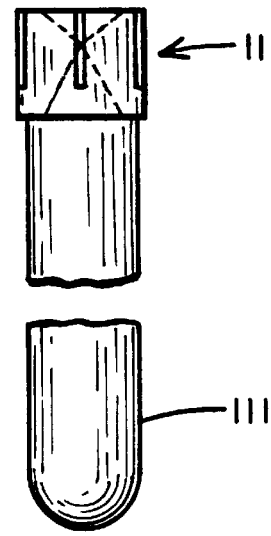
FIG. 10 is a side view of a blood collection tube incorporating an injection site.

Thus, as shown in FIG. 8, the drug transfer spike or key 12, according to the preferred embodiment of the present invention, can be used to penetrate an injection site on a C-Lok 10 to inject a medicant from syringe 64 into a standard catheter, as in FIG. 6, or to an adaptor 92 when drawing the medicant into the syringe 64. It is also contemplated that the injection site 11 can be formed on a blood collection vial or tube 111. Such an arrangement is shown in FIG. 10.

While an annular protrusion or ridge 50 with a smoothly rounded outer surface is the preferred way of forming the locking member, it is also recognized that one or more protrusions having other shapes defined at a predetermined location on key 12 can be used as well. Further, while a positive lock is preferred, such as a protrusion, it is also recognized an annular recess on the shaft of the drug transfer spike 12 can be made to coact with a mating projection within the lumen of the tubular member into which it is inserted. An annular recess in the spike has the disadvantage of possibly weakening it, however.

Further, it is also to be recognized that while a pair of conical recesses are the preferred design for septum 16, the recesses could have identical or different shapes and sizes, and limitation to the upper recess having a volume less than the volume of the lower recess is not to be inferred.

In summary, an injection site comprised of only two pieces is disclosed. It offers the advantage of being inexpensive to manufacture and assemble. The injection site can be adapted to a variety of devices including extension tubes, vial adaptors, Y-connectors, PRN adaptors, single or multi-use medicament containers, blood collection tubes and fluid source bags as well as blood collection tubes. The positive locking member defined along the length of drug transfer spike or key 12 inhibits its accidental retraction, such as by patient movement, while a drug is being injected into a fluid line leading to an indwelling catheter. The uniquely designed septum provides an efficient resealable opening, which opening may be adapted to engage a protrusion 50 on the key to provide a locking arrangement. Finally, the resilient fingers of the injection site facilitate retaining septum 16, yet allowing easy insertion of septum 16 therein. No separate cap is required for securing septum 16 therewithin as in other prior art arrangements.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. A medical drug administering apparatus comprising, in combination:
   (a) a septum having a resilient body and a preformed opening extending at least partially therethrough in an axial direction;
   (b) a housing having a generally cylindrical inlet socket in which said septum is inserted, and having a plurality of adjacent resilient fingers separated from one another, the fingers surrounding the inlet socket for constraining said septum in said inlet socket; and
   (c) an elongated drug transfer spike having a coupling member with a first port at a proximal end thereof adapted to receive an outlet of a syringe and a second port at a distal end of said drug transfer spike adapted to be inserted through said septum's preformed opening, said drug transfer spike having a tubular cannula member with a passageway communicating said first port to said second port, said drug transfer spike having a peripheral surface and locking means disposed on said peripheral surface thereof for cooperating with the resilient fingers for restricting retraction of said drug transfer spike from said septum opening when said spike has been inserted therethrough.

2. The apparatus as specified in claim 1 wherein said locking means comprises a protrusion extending outwardly from a peripheral surface of said spike at a predetermined location between said first and second ports.

3. The apparatus as specified in claim 1 wherein said septum is cylindrical and further characterized in that said opening is defined by first and second generally conical recesses, each having an apex and the apex of the first generally conical recess facing the apex of the second generally conical recess.

4. The apparatus as specified in claim 3 wherein said septum is a thermoplastic resin having a durometer in the range of from 10 to 70 shore A.

5. The apparatus as specified in claim 3 wherein said septum is a liquid injected molded silicone having a durometer in the range of from 10 to 70 shore A.

6. The apparatus as specified in claim 3 wherein the apices of the first and second generally conical recesses are separated from one another by a membrane.

7. The apparatus as specified in claim 6 wherein said apices intersect with one another.

8. The apparatus as specified in claim 1 wherein each of said resilient fingers has a proximal end with an inwardly extending tab at said proximal end for constraining said septum in said inlet socket.

9. The apparatus as specified in claim 8 wherein said locking means comprises an annular projection surrounding said spike adjacent said coupling member, said annular projection cooperating with said inwardly extending tab on said plurality of adjacent resilient fingers.

10. The apparatus as specified in claim 1 wherein said septum occupies less than the entire inlet socket of said housing when inserted therein.

11. The apparatus as specified in claim 1 wherein said septum has a radial dimension greater than the diameter of said cylindrical inlet socket of said housing before insertion therein.

12. A medical drug administering apparatus comprising, in combination:
   (a) a septum having a resilient body and a preformed opening extending at least partially therethrough in an axial direction;
   (b) a housing having a generally cylindrical inlet socket in which said septum is inserted, and having means for constraining said septum in said inlet socket, said constraining means comprising a plurality of resilient, regularly-spaced fingers surrounding said socket with at least a portion of said resilient fingers overlaying the inlet socket; and
   (c) an elongated drug transfer spike having a coupling member with a first port at a proximal end thereof adapted to receive an outlet of a syringe and a second port at a distal end of said drug transfer spike adapted to be inserted through said septum's preformed opening, said drug transfer spike having a tubular cannula member with a passageway communicating said first port to said second port, said drug transfer spike having a peripheral surface and a locking means disposed on said peripheral surface thereof for cooperating with said resilient fingers for restricting retraction of said cannula member of said drug transfer spike from said preformed opening in said septum when said cannula member has been inserted therethrough.

13. The apparatus as specified in claim 12 wherein the locking means comprises an annular protrusion extending outwardly from a peripheral surface of one of said housing and said drug transfer spike for engaging an annular recess on the other of said housing and drug transfer spike.

14. The apparatus as specified in claim 13 wherein said locking means comprises an annular protrusion surrounding said spike adjacent said coupling member, said annular protrusion cooperating with said portion of said regularly spaced fingers overlaying the inlet socket.

15. The apparatus as specified in claim 12 wherein said septum is cylindrical and further characterized in that said opening is defined by first and second generally conical recesses, each having an apex, the apex of the first generally conical recess facing the apex of the second generally conical recess.

16. The apparatus as specified in claim 15 wherein said septum is a thermoplastic resin having a durometer in the range of from 10 to 70, shore A.

17. The apparatus as specified in claim 15 wherein said septum is a liquid injected molded silicon having a durometer in the range of from 10 to 70, shore A.

18. The apparatus as specified in claim 15 wherein the apices of the first and second generally conical recesses are separated from one another by a membrane.

19. The apparatus as specified in claim 18 wherein said apices intersect with one another.

20. The apparatus as specified in claim 12 wherein said septum occupies less than the entire inlet socket of said housing when inserted therein.

21. The apparatus as specified in claim 12 wherein said septum has a radially dimension which is greater than the diameter of said generally cylindrical inlet socket of said housing before insertion therein.

22. The apparatus as specified in claim 12 wherein each of said resilient fingers has a proximal end with an inwardly extending tab at said proximal end for constraining said septum in said inlet socket.

23. The apparatus as specified in claim 22 wherein said locking means comprises an annular projection surrounding said spike adjacent said coupling member, said annular projection cooperating with said inwardly extending tab on said plurality of adjacent resilient fingers.

* * * * *